United States Patent [19]

Mitrovic et al.

[11] 4,123,553

[45] * Oct. 31, 1978

[54] ANTHELMINTICS EFFECTIVE AGAINST LIVER FLUKES

[75] Inventors: Milan Mitrovic, Nutley; Terence J. Hayes, Upper Montclair, both of N.J.

[73] Assignee: Hoffmann-La Roche Inc., Nutley, N.J.

[*] Notice: The portion of the term of this patent subsequent to Jul. 5, 1994, has been disclaimed.

[21] Appl. No.: 775,064

[22] Filed: Mar. 7, 1977

Related U.S. Application Data

[63] Continuation of Ser. No. 724,785, Sep. 20, 1976, Pat. No. 4,034,110.

[51] Int. Cl.$^2$ .................. A61K 31/22; A61K 31/18
[52] U.S. Cl. ................................ 424/311; 424/321
[58] Field of Search ........................ 424/321, 311; 260/556 AR

[56] References Cited

U.S. PATENT DOCUMENTS

| | | | |
|---|---|---|---|
| 3,574,739 | 4/1971 | Wei et al. | 260/556 AR |
| 3,987,199 | 10/1976 | Mrozik | 260/556 AR |

FOREIGN PATENT DOCUMENTS 1,314,919   4/1973   United Kingdom.

*Primary Examiner*—Sam Rosen
*Attorney, Agent, or Firm*—Samuel L. Welt; Bernard S. Leon; R. Hain Swope

[57] ABSTRACT

A method is disclosed for controlling liver fluke infections comprising orally administering to host animals an anthelmintically effective amount of a compound selected from a group of halogen-substituted-benzenesulfonanilides represented by the formula:

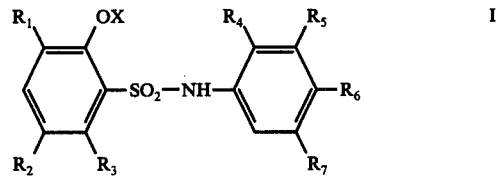

wherein each of $R_1$ and $R_2$ are independently chlorine or bromine, $R_3$ is hydrogen or chlorine and each of $R_4$ through $R_7$ is independently hydrogen, halogen or trifluoromethyl, with the proviso that at least 2 of $R_3$ through $R_7$ is other than hydrogen and X is hydrogen or lower alkanoyl.

12 Claims, No Drawings

ANTHELMINTICS EFFECTIVE AGAINST LIVER FLUKES

RELATED APPLICATIONS

This application is a Continuation of U.S. Patent Application Ser. No. 724,785, filed Sept. 20, 1976, now U.S. Pat. No. 4,034,110, issued July 5, 1977.

BACKGROUND OF THE INVENTION

The halogen-substituted-benzenesulfonanilides of the above generic formula generically are known compounds. Their preparation is taught in French Pat. No. 7,137,123. The disclosed compounds are stated as possessing antibacterial and antifungal activity. Further, certain O-hydroxyhalo-benzenesulfonanilides have been prepared by Schraufstatter et al. (z. Naturtorschung, 16b, 95, 1961) and disclosed as having activity as molluscicides. Earlier work by Foetchius et al (J. Lab. Clin. Med., 32: 1361, 1947) indicates that the introduction of a hydroxyl group into a phenyl ring of a benzenesulfonanilide system results in a decrease of the activity possessed by the compounds. It has now been found in accordance with the present invention that a limited group of O-hydroxy- or O-lower alkanoyloxy-halogen-substituted-benzenesulfonanilides surprisingly possess marked anthelmintic activity in the treatment of liver fluke infections.

DETAILED DESCRIPTION OF THE INVENTION

Compounds represented by the formula

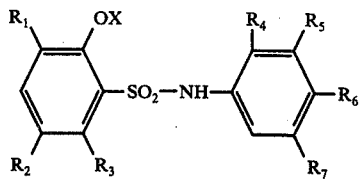

wherein each of $R_1$ and $R_2$ are independently chlorine or bromine. $R_3$ is hydrogen or chlorine and each of $R_4$ through $R_7$ is independently hydrogen, halogen or trifluoromethyl with the proviso that at least 2 and $R_3$ through $R_7$ are other than hydrogen and X is hydrogen or lower alkanoyl possess outstanding anthelmintic activity in the treatment of liver fluke infections.

The common liver fluke which infects sheep and cattle, i.e. *Fasciola hepatica*, is responsible for a considerable economic loss, particularly in those countries of the world where the grazing industry plays a significant part of the economy. The economic loss extends not only to animals lost but to reduction in the production of meat, wool and milk by infected animals. There is a continuing need for compounds which are both highly efficacious and safe in the treatment of liver fluke infections. Such a group of compounds is presented in accordance with the present invention.

The method of treating infections of *Fasciola hepatica* in animals in accordance with the present invention comprises administering to the host animal an anthelmintically effective amount of an anthelmintic composition comprising a suitable carrier and, as the active ingredient, a compound selected from those represented by formula I above.

These compounds have been found to possess an unusually high degree of activity against *Fasciola hepatica*, both mature and immature, with acceptable safety.

A preferred group of compounds falling within the scope of formula I includes 2-hydroxy-2'3,4',5,5'-pentachlorobenzenesulfonanilide; 3,3',4',5,6,-pentachloro-2-hyroxy-benzenesulfonanilide; 2-hydroxy-3,3', 5,5',6-pentachlorobenzenesulfonanilide; 3,3',4',5,5',6-hexachloro-2-hydroxybenzenesulfonanilide; 2-hydroxy-2',3,4',5,5',6-hexachlorobenzenesulfonanilide; 2-hydroxy-2',3,4',5-tetrabromobenzenesulfonanilide; 3,5-dibromo-2-hydroxy-2',4',5'-trichlorobenzenesulfonanilide; 2-acetoxy-2',3,4',5,5',6-hexachlorobenzenesulfonanilide; 2',3,3',4',5,5',6-heptachloro-2-hydroxybenzenesulfonanilide; 2',3,3',4',5,5'-hexachloro-2-hydroxybenzenesulfonanilide; 2',3,3',4',5,6--hexacholoro-2-hydroxybenzenesulfonanilide; 2-hydroxy-2',3,4',5,6-pentachlorobenzenesulfonanilide; and 2',3,4',5,5',6-hexachloro-2-propionoxybenzenesulfonanilide.

A particularly preferred group of compounds in accordance with the invention includes those compounds represented by formula I wherein $R_1$, $R_2$, $R_3$, $R_4$, and $R_6$ are chlorine, $R_5$ is hydrogen, $R_7$ is either hydrogen or chlorine and X is hydrogen, acetoxy or propionoxy.

The term "lower alkanoyl" as utilized herein indicates alkanoyl radicals preferably containing from 2 to 4 carbon atoms with acetoxy and propionoxy being especially preferred. The term "halogen" includes all four halogens with chlorine and bromine being preferred.

The anthelmintic compounds of the present invention can be administered per os, e.g. by tablet, capsule, powder, suspension, granules, bolus, drench and the like, parenterally or dermally. Additionally, they may be compounded as a premix to be admixed with the animal's feed or added to the drinking water. The mode of administration will vary with the type of treatment desired, the host animal, the severity of the infection and the like.

In general, when the anthelmintic compounds of the invention are administered per os, e.g. as a suspension, tablets, or boluses a dosage of from about 1.0 mg to about 100 mg/kg, perferably from about 2 mg to about 20 mg/kg is contemplated. It has been found that a single such dosage is most often sufficient to achieve a complete cure. In some instances, however, it may be advisable to administer the above dosage over a period of a few days in divided doses. It is also within the scope of the invention to administer the above enumerated compounds in the feed or drinking water to control and treat a helmith infection and also in those instances where a divided dosage is desired. In such instances, the concentration of active substance in the feed or drinking water should be sufficient to approximate the above dosages.

Suitable solid dosage units for oral administration, e.g. tablets, capsules, boluses and the like preferably contain from about 0.1 gm to 5.0 gm of the active compounds of the invention. Such solid dosage units will contain from about 15% to about 85% by weight of active substance. Liquid dosage forms, e.g. suspensions will contain the above dosage in the amount of liquid conveniently utilized in veterinary medicine to administer a dose of medication to the animal being treated, e.g. sheep, cattle, etc.

Wherein the active substances of the present invention are to be administered in the form of solid dosage units, e.g. tablets, boluses and the like, such units are compounded by conventional pharmaceutical procedures and contain pharmaceutically acceptable binder and excipient materials such as, for example, starch, lactose, talc, magnesium stearate, methyl cellulose and the like. The compounds of the invention can likewise be filled into soft- or hard-shell gelatin capsules either in undiluted form or with the addition of a sufficient amount of a non-toxic filler substance such as, for example, starch or lactose to achieve a proper capsule fill.

Wherein the active substances of the invention are to be administered in a liquid form, e.g. per os or parenterally, such liquids may be solutions or suspensions and will contain pharmaceutically acceptable adjunct materials recognized in the art. Thus, the liquid preparations may be either aqueous or oil-base preparations and may contain suspending agents, e.g. water-soluble starch derivatives, cellulose derivatives, gums and the like, surface active agents, antifoam agents and the like. Suitable oils include vegetable oils such as, for example, cottenseed oil, safflower oil and the like. The liquid preparations contemplated herein may contain conventional pharmaceutical adjunct materials such as, for example, preservatives, stabilizers, salts for varying osmotic pressure, buffers and the like. Wherein a liquid drench is utilized, it is preferred to prepare a dry predrench composition which contains the active ingredient in up to about 95% by weight in combination with excipients such as described herein, e.g. suspending and/or surface agents. In use, sufficient water is added to the predrench composition to achieve the desired dosage level and the resulting suspension or solution is administered to the animal.

Wherein the active substances of the present invention are to be administered in admixture with a commercial dry feed or ration, a premix or feed supplement is likewise contemplated. Such a premix can contain from about 10% by weight to about 90% by weight active substance. Additionally, such a premix or feed supplement can contain inert carriers or diluents such as, for example, corn meal, germ meal of other cereals, soybean, flour, seed meal, oyster shell flour and the like. A suitable premix can likewise be prepared simply by adding the desired concentration of active substance to a measured quantity of any commercial dry feed or ration. The premix can be added to commercial feed and intimately mixed therewith by conventional techniques to assure a uniform concentration. For convenience in commercial use, it has been found that premixes containing from about 10% by weight to about 20% by weight active substance are preferred with a premix containing about 15% by weight being most preferred. In such premixes as well as in other dosage forms containing the substances disclosed herein, said substances may be combined with other nutritive and/or therapeutically active compounds including other anthelmintically active compounds for therapy against other types of helminth infections which might be present.

The following examples further illustrate the invention.

EXAMPLE 1

The following formulation was homogeneously blended and compressed into boluses. To achieve greater flexibility of dosage, the boluses were scored.

| Ingredient | Grams per Bolus |
| --- | --- |
| 2-Hydroxy-2',3,4',5,5',6-hexachloro-benzenesulfonanilide | 5.05* |
| Pregelatinized Starch | 0.72 |
| Gelatin | 0.15 |
| Alginic Acid | 0.10 |
| Magnesium Stereate | 0.03 |
| Total | 6.05 |

*One percent manufacturing excess.

EXAMPLE 2

A typical feed premix was prepared from the following formulation:

| Ingredient | Percent by Weight |
| --- | --- |
| 2-Hydroxy-2',3,4',5,5',6-hexachloro-benzenesulfonanilide | 15 |
| Microcel E (Calcium Silicate) | 5 |
| Corn Meal | 80 |
| Total | 100 |

The corn meal was placed in a suitable mixer and, while mixing, the Microcel E was slowly added. After addition of the Microcel E was complete and with continued mixing the active ingredient was slowly added, mixing was continued until the mass was homogeneous.

EXAMPLE 3

The below-listed compounds of the present invention were tested orally against *Fasciola hepatica* in mice by the following method. Two control groups were utilized, i.e. an infected unmedicated control group and a group treated with a known anthelmintic agent (standard). The anthelmintic standard utilized was Rafoxanide, i.e. 3'-chloro-4'-(p-chlorophenoxy)-3,5-diiodosalicylanilide. Groups of four mice each were infected with three selected laboratory produced metarcercariae of *F. hepatica*. On day 14 post infection, the animals were weighed and put on standard laboratory feed containing various concentrations of active ingredient. Medicated feed was withdrawn on day 21 post infection at which time the mice were again weighed and the weight of feed consumed during the medication period recorded. On day 28 post infection the mice were sacrificed and necropsied. The liver was examined in situ and pathologic changes recorded. The results are expressed in terms of reduction of pathognostic lesions, i.e. pathognostic pathology as defined by the infected, unmedicated animals and also in a reduction in the number of flukes vs. controls. Wherein two or more of the test animals show an absence of pathognostic lesions, i.e. reduction in the degree of pathologic change of the liver, the compound was considered active at the concentration tested. The results are expressed in Table I.

EXAMPLE 4

In accordance with the procedure of Example 3, the below-listed compounds were tested at various concentrations to determine the concentration at which at least a 50% pathological reduction took place. The results are given in Table II. As in Example 3, a 50% pathological reduction is in comparison to infected, unmedicated controls.

Table I

| Compound Tested | 0.05% by wt. | | | 0.025% by wt. | | | 0.0125% by wt. | | | 0.00625% by wt. | | |
|---|---|---|---|---|---|---|---|---|---|---|---|---|
| | Path. Reduced % | Fluke Reduction % | Activity | Path. Reduced % | Fluke Reduction % | Activity | Path. Reduced % | Fluke Reduction % | Activity | Path. Reduced % | Fluke Reduction % | Activity |
| 3',-chloro-4'-(p-chlorophenoxy)-3,5-diiodosalicylanilide | 100 | 100 | +++ | 100 | 89* | +++ | 100 | 78* | +++ | 100 | 72* | ++ |
| 2-hydroxy-2',3,4',5-tetrabromo-benzene-sulfonanilide | 80 | <70* | ++ | 40 | <70 | + | 40 | <70 | + | 40 | <70 | + |
| 3,3',4',5,6-pentachloro-2-hydroxy-benzene-sulfonanilide | 100 | 100 | +++ | 100 | <70* | +++ | 80 | <70* | ++ | 0 | <70* | — |
| 2-hydroxy-2',3,4',5,5'-pentachlorobenzene-sulfonanilide | 100 | <70 | +++ | 100 | <70 | ++ | 40 | <70 | ++ | 0 | <70 | — |
| 2-hydroxy-3,3',5,5',6-pentachlorobenzene-sulfonanilide | 100 | 100 | +++ | 80 | <70* | ++ | 0 | <70 | + | 0 | <70 | — |
| 2-hydroxy-3,4',5,6,tetrachloro-3'-(trifluoromethyl)-benzenesulfonanilide | 100 | <70 | ++ | 40 | <70 | + | 20 | <70 | — | 20 | <70 | + |
| 4'-bromo-2-hydroxy-3,5,6-trichloro-benzenesulfonanilide | 20 | <70 | + | 0 | <70 | — | 0 | <70 | — | 0 | <70 | — |
| 2-hydroxy-2',3,4',5,5',6-hexachloro-benzenesulfonanilide | 100 | 100 | +++ | 100 | 100 | +++ | 100 | 100 | +++ | 100 | 86* | +++ |
| 3,5-dibromo-2-hydroxy-2',4',5'-trichlorobenzenesulfonanilide | 100 | 89* | +++ | 100 | 100 | +++ | 20 | <70 | + | 20 | <70 | — |

*Flukes smaller than recovered from controls (development inhibited)
+++Marked activity
++Moderate activity
+Slight activity Table II

| Compound Tested | Percent in Diet | Activity* |
|---|---|---|
| 2-acetoxy-2',3,4',5,5',6-hexachlorobenzenesulfonanilide | 0.00625 | + |
| 2',5',-dibromo-2-hydroxy-3,5,6-trichlorobenzenesulfonanilide | 0.1 | + |
| 2',3,3',4',5,5',6-heptachloro-2-hydroxybenzenesulfonanilide | 0.00625 | + |
| 2',3,3',4',5,5'-hexachloro-2-hydroxybenzenesulfonanilide | 0.025 | ± |
| 2',3,3',4',5,6-hexachloro-2-hydroxybenzenesulfonanilide | 0.00625 | + |
| 2-hydroxy-2',3,3',4',5-pentachloro-benzenesulfonanilide | 0.025 | ± |
| 2-hydroxy-2',3,5,5',6-pentachloro-benzenesulfonanilide | 0.1 | + |
| 2-hydroxy-2',3,4',5,6-tetrachloro-benzenesulfonanilide | 0.0125 | + |
| 2',3,4',5,5',6-hexachloro-2-propionoxybenzenesulfonanilide | 0.025 | + |

* "±"indicates 50% pathological reduction
"+"indicates clearly greater than 50% pathological reduction

EXAMPLE 5

The following tests were carried out in vivo against *F. hepatica* infections in sheep.

Groups of two lambs each were exposed orally to 400 selected metacercariae of *F. hepatica*. Four weeks post infection the sheep were given a single oral dosage of various concentrations of: 2-acetoxy-2',3,4',5,5',6-hexachlorobenzenesulfonanilide; 2-hydroxy-2',3,4',5,5',6-hexachlorobenzenesulfonanilide; and, as a standard, 3'-chloro-4'-(p-chlorophenoxy)3,5-diiodosalicylanilide. The compounds were given in 20 ml of a 1.75% aqueous suspension of methyl cellulose. IUC controls received only the vehicle. Two weeks post treatment the animals were necropsied and the livers dissected to obtain total *F. hepatica* counts. The results are given in Table III.

Table III

| Medication/Concentration | No. Animals | No. Live flukes recovered | % Reduction Live flukes |
|---|---|---|---|
| IUC/O* | 2 | 114 193 307 (154) | 0 |
| 2-Hydroxy-2',3,4',5,5',6-hexachlorobenzene-sulfonanilide | | | |
| 20 mg/kg | 2 | 0 0 (0) | 100 |
| 10 mg/kg | 2 | 0 0 (0) | 100 |
| 5 mg/kg | 2 | 5 1 (3) | 98 |
| 2-Acetoxy-2',3,4',5,5',6-hexachlorobenzene-sulfonanilide | | | |
| 20 mg/kg | 2 | 0 0 (0) | 100 |
| 10 mg/kg | 2 | 8 0 (4) | 98 |
| 5 mg/kg | 2 | 50 72 (61) | 71 |
| 4-(O-Chlorophenoxy)-3,4-diiodosalicyl-anilide | | | |
| 10 mg/kg | 2 | 117 91 (104) | 32 |

*Applies to first compound and standard only. A separate control utilized for the second compound showed 212 live flukes recovered (mean for 2 sheep).

EXAMPLE 6

Thirty sheep, approximately 3 months old, were each exposed orally to 200 selected metacercariae of *F. hepatica*. Fourteen weeks after exposure the animals received a single oral dosage of medication suspended in a 1.25% by weight methyl cellulose vehicle. The active compounds of the present invention utilized were: 2-hydroxy-2',3,4',5,5',6-hexachlorobenzenesulfonanilide; 2-acetoxy-2',3,4',5,5',6-hexachlorobenzenesulfonanilide;

and 2′,3,3′,4′,5,6-hexachloro-2-hydroxybenzenesulfonanilide. 3′-Chloro-4′-(p-chlorophenoxy)-3,5-diiodosalicylanilide was again utilized as a standard. IUC controls received only the vehicle. Thirteen days after treatment the animals were necropsied and the livers examined. The results are given in Table IV.

Table IV

| Medication | Concentration (mg/kg) | No. Animals | No. Live Flukes Recovered (mean) | % Reduction Live Flukes |
|---|---|---|---|---|
| IUC | 0 | 2 | 119 162 (141) | 0 |
| 2-Hydroxy-2′,3,4′,5,5′,6-hexachlorobenzenesulfonanilide | 5 | 2 | 0 0 (0) | 100 |
|  | 2 | 2 | 0 3 (1.5) | 98.9 |
|  | 1 | 2 | 76 50 (63) | 55.3 |
|  | 0.5 | 2 | 111 131 (121) | 14.2 |
| 2-Acetoxy-2′3,4′,5,5′,6-hexachlorobenzenesulfonanilide | 5 | 2 | 0 0 (0) | 100 |
|  | 2 | 2 | 8 2 (5) | 96.5 |
|  | 1 | 2 | 80 67 (74) | 47.5 |
|  | 0.5 | 2 | 141 136 (139) | 1.4 |
| 2′,3,3′,4′,5,6-Hexachloro-2-hydroxybenzenesulfonanilide | 5 | 2 | 0 0 (0) | 100 |
|  | 2 | 2 | 15 15 (15) | 89.4 |
|  | 1 | 2 | 46 56 (51) | 63.8 |
|  | 0.5 | 2 | 110 113 (112) | 20.6 |
| 3′-Chloro-4′-(p-chlorophenoxy)-3,5-diiodosalicylanilide | 5 | 2 | 0 0 (0) | 100 |
|  | 1 | 2 | 92 35 (64) | 54.6 |

EXAMPLE 7

A total of twelve sheep were each exposed to 100 selected metacercariae of F. hepatica. Fourteen weeks post infection 5 of the sheep received 2-hydroxy-2′,3,4′,5-tetrabromobenzenesulfonanilide and, as a standard, 3′-chloro-4′-(p-chlorophenoxy)-3,5-diiodosalicylanilide, respectively. At sixteen weeks, another group of three sheep received the same medication. Two sheep served as infected, unmedicated controls (IUC) for each time period. Eight days after treatment the sheep were necropsied.

A third group of seven sheep were similarly exposed to 100 metacercariae of F. hepatica twice at an interval of ten weeks. Six weeks after the second exposure, i.e. 16 weeks after the initial exposure, four of the sheep were treated with 2-hydroxy-2′,3,4′,5-tetrabromobenzenesulfonanilide, one received the standard and two served as infected, unmedicated controls. Nine days later the sheep, which had both mature and immature flukes, were necropsied.

A final group of four sheep were exposed to 100 metacercariae each of F. hepatica. Eight weeks after exposure, the animals were treated with 2-hydroxy-2′,3,4′,5-tetrabromobenzenesulfonanilide. Eight days after treatment the animals were necropsied.

In all instances the animals received a single intraruminal injection of active compound suspended in 0.5% or 1% by weight methyl cellulose U.S.P. in water. Fluke recoveries are given in Table V.

Table V

| Compound | Dose (mg/kg) | No. Sheep | Time treated post infection | Live F. hepatica recovered No. flukes Immature | No. flukes Mature | % Reductions Immature | % Reductions Mature |
|---|---|---|---|---|---|---|---|
| IUC | — | 2 | 16 wk | — | 101 | — | 0 |
| Standard* | 10 | 2 | 16 wk | — | 0 | — | 100 |
| 2-Hydroxy-2′,3,4′,5-tetrabromobenzenesulfonanilide | 100 | 1 | 16 wk | — | 0 | — | 100 |
| IUC | — | 2 | 14 wk | — | 79 | — | 0 |
| Standard* | 10 | 1 | 14 wk | — | 0 | — | 100 |
| 2-Hydroxy-2′,3,4′,5-tetrabromobenzenesulfonanilide | 10 | 2 | 14 wk | — | 3** | — | 96 |
|  | 25 | 2 | 14 wk | — | 0 | — | 100 |
| IUC | — | 2 | 6,16 wk | 71 | 110 | 0 | 0 |
| Standard* | 10 | 1 | 6,16 wk | 3 | 0 | 92 | 100 |
| 2-Hydroxy-2′,3,4′,5-tetrabromobenzenesulfonanilide | 20 | 2 | 6,16 wk | 37 | 1 | 48 | 99 |
|  | 40 | 2 | 6,16 wk | 17** | 0 | 76 | 100 |
| IUC | — | 2 | 8 wk | 92 | — | 0 | — |
| 2-Hydroxy-2′,3,4′,5-tetrabromobenzenesulfonanilide | 40 | 2 | 8 wk | 0 | — | 100 | — |

*4-(p-chlorophenoxy)-3,5-diiodosalicylanilide
**Stunted (small)

EXAMPLE 8

Fourteen mixed breed calves were each exposed orally to 600 selected metacercariae of F. hepatica. Fourteen weeks post exposure, the animals were given a single oral dose of various concentrations of 2-hydroxy-2′,3,4′,5,5′,6-hexachlorobenzenesulfonanilide and, as a standard, 3′-chloro-4′-(p-chlorophenoxy)-3,5-diiodosalicylanilide. IUC controls received no medication. Thirteen days after treatment, the calves were sacrificed and the flukes recovered by dissection of the liver. The results are given in Table VI.

Table VI

| Medication | Dose (mg/kg) | No. Animals | No. Live flukes Recovered (mean) | % Reduction Live flukes |
|---|---|---|---|---|
| IUC | — | 2 | 108 166 (137) | 0 |
| 2-Hydroxy-2′,3,4′,5,5′,6-hexachlorobenzenesulfonanilide | 5 | 2 | 2 3 (2.5) | 98 |
|  | 4 | 2 | 24 54 (39) | 72 |
|  | 3 | 2 | 102 41 (72) | 48 |
|  |  |  | 119 |  |

Table VI-continued

| Medication | Dose (mg/kg) | No. Animals | No. Live flukes Recovered (mean) | % Reduction Live flukes |
|---|---|---|---|---|
| 3'-Chloro-4'-(p-chlorophenoxy)-3,5-diiodosalicylanilide | 2 | 2 | 144 (132) 75 | 4 |
|  | 5 | 2 | 22 (49) | 65 |
|  | 2 | 2 | 220 75 (148) | 0 |

We claim:

1. A composition for parenteral administration to an animal for treatment of *Fasciola hepatica* infections which comprises a non-toxic carrier material suitable for parenteral administration and an effective amount of an anthelmintic compound represented by the formula

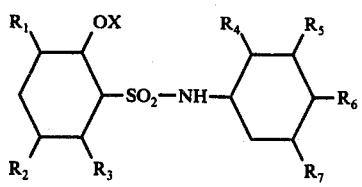

wherein each of $R_1$ and $R_2$ are independently chlorine or bromine, $R_3$ is hydrogen or chlorine and each of $R_4$ through $R_7$ is independently hydrogen, halogen or trifluoromethyl, with the proviso that at least 2 of $R_3$ through $R_7$ is other than hydrogen and X is hydrogen or lower alkanoyl.

2. A composition in accordance with claim 1 wherein said anthelmintic compound is selected from the group consisting of 2-hydroxy-2',3,4',5,5'-pentachlorobenzenesulfonanilide; 3,3',4',5,6-pentachloro-2-hydroxybenzenesulfonanilide; 2-hydroxy-3,3',5,5',6-pentachlorobenzenesulfonanilide; 3,3',4',5,5',6-hexachloro-2-hydroxybenzensulfonanilide; 2-hydroxy-2',3,4',5,5',6-hexachlorobenzenesulfonanilide; 2-hydroxy-2',3,4',5-tetrabromobenzenesulfonanilide; 3,5-dibromo-2-hydroxy-2',4',5'-trichlorobenzenesulfonanilide; 2-acetoxy-2',3,4',5,5',6-hexachlorobenzenesulfonanilide; 2',3,3',4,5,5',6-heptachloro-2-hydroxybenzenesulfonanilide; 2',3,3',4',5,5'-hexachloro-2-hydroxybenzenesulfonanilide; 2',3,3',4',5,6-hexachloro-2-hydroxybenzenesulfonanilide; 2-hydroxy-2',3,4',5,6-pentachlorobenzenesulfonanilide; and 2,3,4',5,5',6-hexachloro-2-propionoxybenzenesulfonanilide.

3. A composition in accordance with claim 1 wherein in said formula $R_1$, $R_2$, $R_3$, $R_4$ and $R_6$ are chlorine, $R_5$ is hydrogen, $R_7$ is hydrogen or chlorine and X is hydrogen, acetoxy or propionoxy.

4. A composition in accordance with claim 3 wherein said anthelmintic compound is 2-hydroxy-2',3,4',5,6-pentachlorobenzenesulfonanilide.

5. A composition in accordance with claim 3 wherein said anthelmintic compound is 2-acetoxy-2',3,4',5,5',6-hexachlorobenzenesulfonanilide.

6. A composition in accordance with claim 3 wherein said anthelmintic compound is 2',3,4',5,5',6-hexachloro-2-propionoxybenzenesulfonanilide.

7. A composition in accordance with claim 3 wherein said anthelmintic compound is 2-hydroxy-2',3,4',5,5',6-hexachlorobenzenesulfonanilide.

8. A composition for oral administration to an animal in the form of a bolus for treatment of *Fasciola hepatica* infections said bolus comprising suitable non-toxic carrier material and an effective amount of an anthelmintic compound represented by the formula

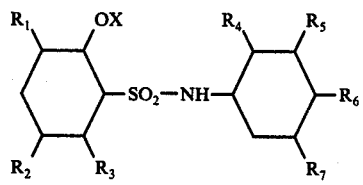

wherein each of $R_1$ and $R_2$ are independently chlorine or bromine, $R_3$ is hydrogen or chlorine and each of $R_4$ through $R_7$ is independently hydrogen, halogen or trifluoromethyl, with the proviso that at least 2 of $R_3$ through $R_7$ are other than hydrogen and X is hydrogen or lower alkanoyl.

9. A composition in accordance with claim 8 wherein said anthelmintic compound is selected from the group consisting of 2-hydroxy-2',3,4',5,5'-pentachlorobenzenesulfonanilide; 3,3',4',5,6-pentachloro-2-hydroxybenzenesulfonanilide; 2-hydroxy-3,3',5,5',6-pentachlorobenzenesulfonanilide; 3,3',4',5,5',6-hexachloro-2-hydroxybenzenesulfonanilide; 2,hydroxy-2',3,4',5,5',6-hexachlorobenzenesulfonanilide; 2-hydroxy-2',3,4',5-tetrabromobenzenesulfonanilide; 3,5-dibromo-2-hydroxy-2',4',5'-trichlorobenzenesulfonanilide; 2-acetoxy-2',3,4',5,5',6-hexachlorobenzenesulfonanilide; 2',3,3',4,5,5',6-heptachloro-2-hydroxybenzenesulfonanilide; 2',3,3',4',5,5'-hexachloro-2-hydroxybenzenesulfonanilide; 2',3,3',4',5,6hexachloro-2-hydroxybenzenesulfonanilide; 2-hydroxy-2',3,4',5,6-pentachlorobenzenesulfonanilide; and 2,3,4',5,5',6-hexachloro-2-propionoxybenzenesulfonanilide.

10. A composition in accordance with claim 8 wherein in said formula $R_1$, $R_2$, $R_3$, $R_4$ and $R_6$ are chlorine, $R_5$ is hydrogen, $R_7$ is hydrogen or chlorine and X is hydrogen, acetoxy or propionoxy.

11. A composition in accordance with claim 10 wherein said anthelmintic compound is 2-hydroxy-2',3,4',5,6-pentachlorobenzenesulfonanilide.

12. A composition in accordance with claim 10 wherein said anthelmintic compound is 2-acetoxy-2',3,4',5,5',6-hexachlorobenzenesulfonanilide.

* * * * *